United States Patent

Lefoulon et al.

[11] Patent Number: 6,143,789
[45] Date of Patent: Nov. 7, 2000

[54] NAPHTHALENE COMPOUNDS

[75] Inventors: François Lefoulon; Luc Demuynck, both of Orleans; Daniel Lesieur, Gondecourt; Patrick Depreux, Armentieres; Caroline Bennejean, Charenton-le-Pont; Pierre Renard, Versailles; Philippe Delagrange, Issy les Moulineaux, all of France

[73] Assignee: Adir et Compagnie, Courbevoie, France

[21] Appl. No.: 09/199,531

[22] Filed: Nov. 25, 1998

[30] Foreign Application Priority Data

Nov. 28, 1997 [FR] France .................. 97 14975

[51] Int. Cl.⁷ .................. A61K 31/16; C07C 233/05
[52] U.S. Cl. .................. 514/630; 514/357; 514/438; 514/461; 514/520; 514/613; 514/624; 546/337; 549/76; 549/496; 558/414; 564/190; 564/219; 564/123
[58] Field of Search .................. 514/630, 419, 514/443, 465, 625, 626, 624, 613, 461, 438, 357, 520; 564/219, 190, 123; 549/55, 467, 496, 76; 546/337; 558/414

[56] References Cited

U.S. PATENT DOCUMENTS

| | | | |
|---|---|---|---|
| 5,318,994 | 6/1994 | Andreux et al. | 514/613 |
| 5,604,261 | 2/1997 | Langlois et al. | 514/630 |
| 5,668,180 | 9/1997 | Lesieur et al. | 514/630 |
| 5,731,352 | 3/1998 | Lesieur et al. | 514/630 |

*Primary Examiner*—Shailendra Kumar

*Attorney, Agent, or Firm*—The Firm of Gordon W. Hueschen

[57] ABSTRACT

Compound of formula (I):

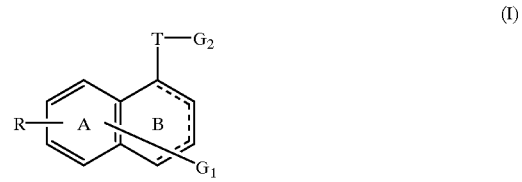

wherein:
T represents alkylene,
A and B together form a naphthalene, dihydronaphthalene, or tetrahydronaphthalene group,
R represents hydrogen, hydroxy, R' or OR', R' being as defined in the description,
$G_1$ represents halogen, a radical $R_1$ or a group —O—CO—$R_1$, $R_1$ being as defined in the description,
$G_2$ represents a group selected from:

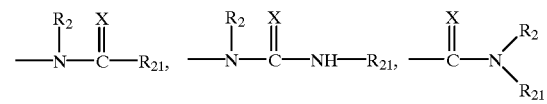

X, $R_2$ and $R_{21}$ being as defined in the description, and medicinal products containing the same which are useful in the treatment of a condition related to the melatoninergic system.

23 Claims, No Drawings

NAPHTHALENE COMPOUNDS

The present invention relates to new compounds having a naphthalene structure.

DESCRIPTION OF THE PRIOR ART

Patent Specifications EP 447 285, EP 530 087 and EP 562 956 describe naphthylalkyl-amide, naphthylalkylurea and naphthylalkylthiourea compounds having valuable pharmacological properties by virtue of their affinity for melatonin receptors and their agonist or antagonist character. All those compounds are characterised by the presence of a single substituent on the ring structure carrying the alkylamide or alkylurea chain. Application WO 9706140 describes closely related melatoninergic ligands that are acylated on the main ring structure carrying the alkylamide chain.

BACKGROUND OF THE INVENTION

Many studies in the last ten years have shown the key role of melatonin (N-acetyl-5-methoxytryptamine) in many physiopathological phenomena and in the control of circadian rhythm. Its half-life is, however, quite short owing to its being rapidly metabolised. It is thus very valuable to be able to provide the clinician with melatonin analogues that are metabolically more stable, that have an agonist or antagonist character and which may be expected to have a therapeutic action that is superior to that of the hormone itself.

In addition to their beneficial action on circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272) and analgesic properties (Pharmacopsychiat., 1987, 20, pp. 222–223), and also for the treatment of Parkinson's disease (J. Neurosurg. 1985, 63, pp. 321–341) and Alzheimer's disease (Brain Research, 1990, 528, pp. 170–174). Those compounds have also shown activity on certain cancers (Melatonin—Clinical Perspectives, Oxford University Press, 1988, pp. 164–165) ovulation (Science 1987, 227, pp. 714–720), diabetes (Clinical Endocrinology, 1986, 24 pp. 359–364), and in the treatment of obesity (International Journal of Eating Disorders, 1996, 20 (4), pp. 443–446).

Those various effects take place via the intermediary of specific melatonin receptors. Molecular biology studies have shown the existence of a number of receptor sub-types that can bind that hormone (Trends Pharmacol. Sci., 1995, 16, p. 50; WO 97.04094). It has been possible to locate some of those receptors and to characterise them for different species, including mammals. In order to be able to understand the physiological functions of those receptors better, it is very useful to have available specific ligands. Moreover, by interacting selectively with one or other of those receptors, such compounds can be excellent medicaments for the clinician in the treatment of pathologies associated with the melatoninergic system, some of which have been mentioned above.

The compounds of the present invention have a novel structure that is characterised by a naphthylalkyl-amide, -thioamide, -urea or -thiourea ring structure that is partially hydrogenated or unhydrogenated and has two substituents on the main ring structure. Surprisingly, that structure imparts to the compounds very great affinity for melatonin receptors and selectivity for one or other of the receptor sub-types.

DETAILED DESCRIPTION OF THE INVENTION

The invention relates to compounds of formula (I)

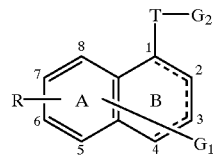

wherein:

the A and B rings together form a naphthalene, 1,2-dihydronaphthalene, 2,3-dihydronaphthalene, 1,4-dihydronaphthalene or tetrahydronaphthalene group, T represents a linear or branched $(C_1-C_6)$alkylene chain optionally substituted by one or more linear or branched $(C_1-C_6)$alkyl, hydroxy, linear or branched $(C_1-C_6)$alkoxy, carboxy and/or linear or branched $(C_1-C_6)$alkoxycarbonyl groups, R represents a hydrogen atom, a hydroxy group, a radical R' or a group OR', R' representing an optionally substituted linear or branched $(C_1-C_6)$alkyl, optionally substituted linear or branched $(C_2-C_6)$alkenyl, optionally substituted linear or branched $(C_2-C_6)$alkynyl, optionally substituted $(C_3-C_7)$cycloalkyl, optionally substituted $(C_4-C_7)$cycloalkenyl, linear or branched trihalo$(C_1-C_6)$alkylsulphonyl, optionally substituted aryl, optionally substituted biphenyl or optionally substituted heteroaryl group, or R forms, with two adjacent carbon atoms of the A ring, a 5- to 7-membered ring that is saturated, unsaturated or partially saturated and contains an oxygen atom, that ring being optionally substituted by one or more groups selected from linear or branched $(C_1-C_6)$alkyl, linear or branched $(C_1-C_6)$ alkoxy, carboxy, linear or branched $(C_1-C_6)$ alkoxycarbonyl group, hydroxy and oxo, $G_1$ represents a halogen atom (and in that case is bonded to any of the junctions of the B ring), a linear or branched trihalo$(C_1-C_6)$alkylsulphonyloxy, carboxy, formyl or cyano group, a radical $R_1$ or a group —O—CO—$R_1$, $R_1$ representing an optionally substituted linear or branched $(C_1-C_6)$alkyl, optionally substituted linear or branched $(C_2-C_6)$alkenyl, optionally substituted linear or branched $(C_2-C_6)$alkynyl, optionally substituted $(C_3-C_7)$cycloalkyl, optionally substituted aryl, optionally substituted biphenyl or optionally substituted heteroaryl group, $G_2$ represents a group selected from:

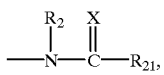

(G$_{20}$)

(G$_{21}$)

-continued

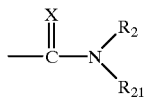

(G₂₂)

wherein:

X represents an oxygen or sulphur atom, $R_2$ represents a hydrogen atom or a linear or branched ($C_1$–$C_6$)alkyl group, $R_{21}$ represents an optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted ($C_3$–$C_7$)cycloalkyl, optionally substituted heteroaryl, optionally substituted aryl or optionally substituted biphenyl group, with the proviso that:

when $G_2$ represents a group $G_{22}$, then $G_1$ represents a linear or branched trihalo ($C_1$–$C_6$)alkylsulphonyloxy group, an optionally substituted heteroaryl group different from pyridyl, a linear or branched ($C_1$–$C_6$)alkyl group substituted by an optionally substituted heteroaryl group different from pyridyl, or a group O—CO—$R_1$, with $R_1$ being as defined hereinbefore, when $G_2$ represents a group $G_{20}$ or $G_{21}$, and $G_1$, which is other than an optionally substituted heteroaryl group, is bonded to any of the junctions of the A ring whilst R represents a hydrogen atom, or is bonded to any of the junctions of the B ring, then T represents an optionally substituted methylene or ethylene chain, when A and B together form a naphthalene group, R being other than a group OR' wherein R' is a linear or branched ($C_2$–$C_6$)alkenyl or linear or branched ($C_2$–$C_6$) alkynyl group, and $G_1$ is bonded to any of the junctions of the B ring, then $G_1$ is other than an optionally substituted linear or branched ($C_1$–$C_6$)alkyl, optionally substituted linear or branched ($C_2$–$C_6$)alkenyl or optionally substituted linear or branched ($C_2$–$C_6$) alkynyl group and other than a group —O—CO—$R_1$, $R_1$ being as defined hereinbefore, when R represents a group OR', R' being as defined hereinbefore, then $G_1$, if it is bonded to any of the junctions of the A ring, is other than a linear or branched ($C_1$–$C_6$)alkyl optionally substituted by one or more halogen atoms hydroxy or linear or branched ($C_1$–$C_6$)alkoxy groups, and other than linear or branched ($C_2$–$C_6$)alkenyl or linear or branched ($C_2$–$C_6$) alkynyl group, when A and B together form a tetrahydronaphthalene group, $G_1$ is bonded in the 3- and 4-position of that ring structure, when $G_2$ represents a group $G_{20}$ or $G_{21}$, A and B together form a naphthalene group or a tetrahydronaphthalene group and R represents a hydrogen atom, then $G_1$, if it is bonded to any of the junctions of the A ring, is other than a linear or branched ($C_1$–$C_6$)alkyl group optionally substituted by one or more halogen atoms or hydroxy or linear or branched ($C_1$–$C_6$)alkoxy groups, other than a linear or branched ($C_1$–$C_6$)alkyl group substituted by a ($C_3$–$C_7$)cycloalkyl group optionally substituted by one or more halogen atoms, and other than a ($C_3$–$C_7$) cycloalkyl group optionally substituted by one or more halogen atoms, when $G_2$ represents a group $G_{20}$ in which X is an oxygen atom and $R_{21}$ represents a phenyl group, and A and B together form a 1,2-dihydronaphtalen group, then $G_1$, if it is bonded in the 2-position of that ring structure, is other than a linear or branched ($C_1$–$C_6$)alkyl group, when T represents an ethylene group and $G_2$ represents a group $G_{21}$ wherein X represents a sulphur atom, then $R_{21}$ is other than an optionally substituted aryl group, the term "aryl" denoting a phenyl or naphthyl group, the term "heteroaryl" denoting a mono- or bi-cyclic group having from 4 to 11 ring members, being saturated or unsaturated and containing from 1 to 4 hetero atoms selected from nitrogen, oxygen and sulphur, it being understood that:

the term "optionally substituted" applied to the terms "alkyl", "alkenyl", "alkynyl", "cycloalkyl" and "cycloalkenyl" means that those groups are substituted by one or more halogen atoms, and/or ($C_3$–$C_7$) cycloalkyl, hydroxy, linear or branched ($C_1$–$C_6$)alkoxy, optionally substituted aryl and/or optionally substituted heteroaryl groups, the term "optionally substituted" applied to the terms "aryl", "biphenyl" and "heteroaryl" means that those groups are substituted by one or more halogen atoms, and/or linear or branched ($C_1$–$C_6$)alkyl, linear or branched trihalo($C_1$–$C_6$)alkyl, hydroxy, linear or branched ($C_1$–$C_6$)alkoxy and/or nitro groups and/or amino groups (optionally substituted by one or two identical or different linear or branched ($C_1$–$C_6$)alkyl groups) and/or cyano, carboxy and/or linear or branched ($C_1$–$C_6$)alkylcarbonyl groups and/or aminocarbonyl groups (optionally substituted by one or two identical or different linear or branched ($C_1$–$C_6$)-alkyl groups), their enantiomers, diastereoisomers, and addition salts thereof with a pharmaceutically acceptable acid or base.

Compounds of formula (1) having one or more asymmetrical carbon atoms that are obtained in the form of a mixture can be subjected to separation according to conventionally used techniques, and the resulting enantiomers and/or diastereoisomers form part of the invention in the same way as the compounds of formula (I).

Amongst the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc.

Amongst the pharmaceutically acceptable bases there may be mentioned by way of non-limiting example sodium hydroxide, potassium hydroxide, triethylamine, tert-butylamine, etc.

The present invention relates advantageously to compounds of formula (I) wherein:

the A and B rings together form a naphthalene group,

T represents a linear or branched ($C_1$–$C_6$)alkylene chain,

R represents a hydrogen atom, a hydroxy group, a radical R' or a group OR', R' representing an optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted ($C_3$–$C_7$)cycloalkyl, optionally substituted ($C_4$–$C_7$)cycloalkenyl, linear or branched trihalo($C_1$–$C_6$)alkylsulphonyl, optionally substituted aryl, optionally substituted biphenyl or optionally substituted heteroaryl group, $G_1$, which is bonded to any of the junctions of the B ring, represents a halogen atom or a linear or branched trihalo($C_1$–$C_6$)alkylsulphonyloxy, carboxy, formyl, cyano, optionally substituted aryl, optionally substituted heteroaryl or optionally substituted biphenyl group, $G_2$ represents a group selected from:

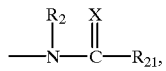
($G_{20}$)

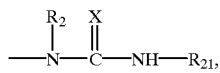
($G_{21}$)

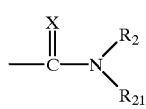
($G_{22}$)

wherein:

X represents an oxygen or sulphur atom, $R_2$ represents a hydrogen atom or a linear or branched ($C_1$–$C_6$)alkyl group, $R_{21}$ represents an optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted ($C_3$–$C_7$)cycloalkyl, optionally substituted heteroaryl, optionally substituted aryl or optionally substituted biphenyl group.

A further advantageous embodiment of the present invention relates to compounds of formula (I) wherein:

the A and B rings together form a tetrahydronaphthalene group,

T represents a linear or branched ($C_1$–$C_6$)alkylene chain,

R represents a hydrogen atom, a hydroxy group, a radical R' or a group OR', R' representing an optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted ($C_3$–$C_7$)cycloalkyl, optionally substituted ($C_4$–$C_7$)cycloalkenyl, linear or branched trihalo($C_1$–$C_6$)alkylsulphonyl, optionally substituted aryl, optionally substituted biphenyl or optionally substituted heteroaryl group, $G_1$, which is bonded in the 3- or 4-position of the B ring, represents a halogen atom or a linear or branched trihalo($C_1$–$C_6$)alkylsulphonyloxy, carboxy, formyl, cyano, optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted ($C_3$–$C_7$)cycloalkyl, optionally substituted aryl, optionally substituted biphenyl or optionally substituted heteroaryl group, $G_2$ represents a group selected from:

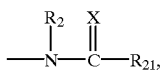
($G_{20}$)

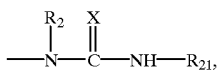
($G_{21}$)

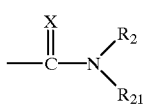
($G_{22}$)

wherein:

X represents an oxygen or sulphur atom, $R_2$ represents a hydrogen atom or a linear or branched ($C_1$–$C_6$)alkyl group, $R_{21}$, represents an optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted ($C_3$–$C_7$)cycloalkyl, optionally substituted heteroaryl, optionally substituted aryl or optionally substituted biphenyl group.

A further advantageous embodiment of the present invention relates to compounds of formula (I) wherein:

the A and B rings together form a naphthalene group,

T represents a linear or branched ($C_1$–$C_6$)alkylene chain,

R represents a hydrogen atom, $G_1$, which is bonded to any of the positions of the A ring, represents a linear or branched trihalo($C_1$–$C_6$) alkylsulphonyloxy, carboxy, formyl, cyano, optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted aryl, optionally substituted biphenyl or optionally substituted heteroaryl group, $G_2$ represents a group selected from:

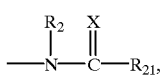
($G_{20}$)

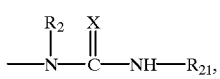
($G_{21}$)

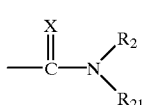
($G_{22}$)

wherein:

X represents an oxygen or sulphur atom, $R_2$ represents a hydrogen atom or a linear or branched ($C_1$–$C_6$)alkyl group, $R_2$ represents an optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted ($C_3$–$C_7$)cycloalkyl, optionally substituted heteroaryl, optionally substituted aryl or optionally substituted biphenyl group.

The preferred compounds of the invention are those wherein T represents an alkylene chain having 2 or 3 carbon atoms.

In the compounds of the invention, the group R is preferably attached in the 7-position of the bicyclic ring structure.

In the compounds of the invention, preferably the group $G_1$ is attached in the 3-position of the bicyclic ring structure or in the 7-position of that same ring structure.

The preferred $G_1$ groups of the invention are optionally substituted aryl (for example phenyl) groups and optionally substituted heteroaryl (for example furyl, thienyl, pyridyl) groups.

In the compounds of the invention, especially R represents a group R' or OR', wherein R' represents a linear or branched ($C_1$–$C_6$)alkyl group (for example a methyl group) or a linear or branched ($C_2$–$C_6$)alkenyl group.

The preferred $G_2$ groups of the invention are those wherein X represents an oxygen atom, $R_2$ represents a hydrogen atom and $R_{21}$ represents a group selected from linear or branched ($C_1$–$C_6$)alkyl optionally substituted by one or more halogen atoms, linear or branched ($C_2$–$C_6$) alkenyl, linear or branched ($C_2$–$C_6$)alkynyl and ($C_3$–$C_7$) cycloalkyl. Preferably $G_2$ represents a group $G_{20}$ or $G_{22}$.

More preferably, the present invention relates to compounds of formula (I) wherein A and B together form a naphthalene group, T represents a linear or branched ($C_1$–$C_6$)alkylene chain, R, which is attached in the 7-position of the bicyclic ring structure, represents a group R' or OR', R' being a linear or branched ($C_1$–$C_6$)alkyl or linear or branched ($C_2$–$C_6$)alkenyl group, $G_1$, which is attached in the 3-position of the bicyclic ring structure, represents a halogen atom or a linear or branched trihalo ($C_1$–$C_6$)alkylsulphonyloxy, carboxy, formyl, cyano, optionally substituted aryl or optionally substituted heteroaryl group, and $G_2$ represents a group $G_{20}$ or $G_{22}$ wherein X represents an oxygen atom, $R_2$ represents a hydrogen atom, and $R_{21}$ represents a group selected from linear or branched ($C_1$–$C_6$)alkyl optionally substituted by one or more halogen atoms, linear or branched ($C_2$–$C_6$)alkenyl, linear or branched ($C_2$–$C_6$)alkynyl and ($C_3$–$C_7$)cycloalkyl.

A further highly advantageous embodiment of the invention relates to compounds of formula (I) wherein A and B together form a tetrahydronaphthalene group, T represents a linear or branched ($C_1$–$C_6$)alkylene chain, R, which is attached in the 7-position of the bicyclic ring structure, represents a group R' or OR', R' being a linear or branched ($C_1$–$C_6$)alkyl or linear or branched ($C_2$–$C_6$)alkenyl group, $G_1$, which is attached in the 3-position of the bicyclic ring structure, represents an optionally substituted aryl or optionally substituted heteroaryl group, and $G_2$ represents a group selected from $G_{20}$ and $G_{22}$ wherein X represents an oxygen atom, $R_2$ represents a hydrogen atom, and $R_{21}$ represents a group selected from linear or branched ($C_1$–$C_6$)alkyl optionally substituted by one or more halogen atoms, linear or branched ($C_2$–$C_6$)alkenyl, linear or branched ($C_2$–$C_6$) alkynyl and ($C_3$–$C_7$)cycloalkyl.

A further highly advantageous embodiment of the invention relates to compounds of formula (I) wherein A and B together form a naphtalene group, T represents a linear or branched ($C_1$–$C_6$)alkylene chain, R represents a hydrogen atom, $G_1$, which is attached in the 7-position of the bicyclic ring structure, represents an optionally substituted aryl or optionally substituted heteroaryl group, and $G_2$ represents a group selected from $G_{20}$ and $G_{22}$ wherein X represents an oxygen atom, $R_2$ represents a hydrogen atom, and $R_{21}$ represents a group selected from linear or branched ($C_1$–$C_6$) alkyl optionally substituted by one or more halogen atoms, linear or branched ($C_2$–$C_6$)alkenyl, linear or branched ($C_2$–$C_6$)alkynyl and ($C_3$–$C_7$)-cycloalkyl.

Amongst the preferred compounds of the invention there may be mentioned most especially the following compounds:

N-[2-(7-methoxy-3-phenyl-1-naphthyl)ethyl]acetamide
N-{2-[3-(2-furyl)-7-methoxy-1-naphthyl]ethyl}acetamide
N-{2-[7-methoxy-3-(4-pyridyl)-1-naphthyl] ethyl}acetamide
N-{2-[7-methoxy-3-(3-trifluoromethylphenyl)-1-naphthyl] ethyl}acetamide
N-{2-[7-methoxy-3-(3-aminophenyl)-1-naphthyl] ethyl}acetamide
N-[2-(7-phenyl-1-naphthyl)ethyl]acetamide
N-{2-[7-(4-methylphenyl)-1-naphthyl]ethyl}acetamide
N-[2-(7-methoxy-3-phenyl-1,2,3,4-tetrahydro-1-naphthyl) ethyl]acetamide
N-{2-[7-methoxy-3-(3-trifluoromethylphenyl)-1,2,3,4-tetrahydro-1-naphthyl]ethyl}acetamide.

The invention relates also to a process for the preparation of compounds of formula (I), characterised in that there is used as starting material a compound of formula (II/a)

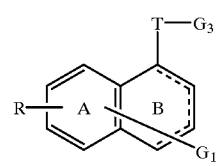

(II/a)

wherein T, A, B, R and $G_1$ are as defined for formula (I) and $G_3$ represents a group —COOH or —NH—$R_2$, $R_2$ being as defined for formula (I), which, when $G_3$ represents a group —NH—$R_2$, is reacted with a) an acyl chloride of formula (III):

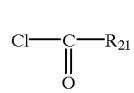

(III)

wherein $R_{21}$ is as defined for formula (I),
or with a corresponding acid anhydride (mixed or symmetrical),
to yield a compound of formula (I/a):

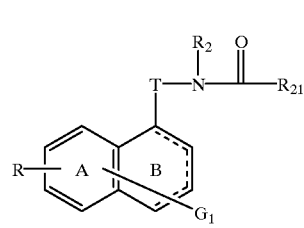

(I/a)

which is a particular case of the compounds of formula (I) wherein T, A, B, R, $R_2$, $R_{21}$ and $G_1$ are as defined for formula (I), which compound of formula (I/a) can be subjected to a thionisation agent, for example Lawesson's reagent, to obtain a compound of formula (I/b):

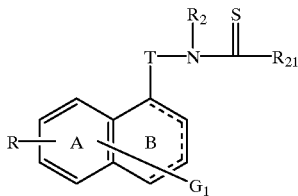
(I/b)

which is a particular case of the compounds of formula (I) wherein T, A, B, R, $R_2$, $R_{21}$ and $G_1$ are as defined hereinbefore, b) an iso(thio)cyanate of formula (IV):

(IV)

wherein X and $R_{21}$ are as defined for formula (I), to yield a compound of formula (I/c):

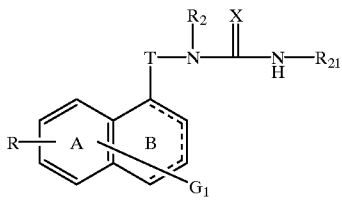
(I/c)

which is a particular case of the compounds of formula (I) wherein T, A, B, R, $R_2$, $R_{21}$, X and $G_1$ are as defined hereinbefore,
or,
when $G_1$ represents a carboxy group, is reacted with a compound of formula (V):

(V)

wherein $R_2$ and $R_{21}$ are as defined for formula (I), to yield a compound of formula (I/d):

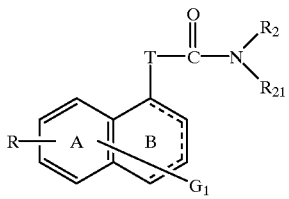
(I/d)

which is a particular case of the compounds of formula (I) wherein T, A, B, R, $R_2$, $R_{21}$ and $G_1$ are as defined hereinbefore,
which compound (I/d) can be subjected to a thionisation agent, for example Lawesson's reagent, to obtain a compound of formula (I/e):

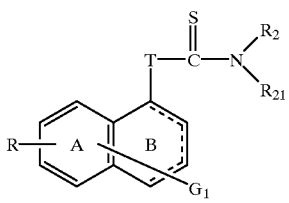
(I/e)

which is a particular case of the compounds of formula (I) wherein T, A, B, R, $R_2$, $R_{21}$ and $G_1$ are as defined hereinbefore, which compounds (I/a), (I/b), (I/c), (I/d) and (I/e), constituting the totality of the compounds of formula (I), can be purified, if necessary, according to a conventional purification technique, are separated, where appropriate, into their isomers according to a conventional separation technique, are converted, if desired, into addition salts thereof with a pharmaceutically acceptable acid or base.

The invention relates also to a process for the preparation of compounds of formula (I), characterised in that there is used as starting material a compound of formula (II/b):

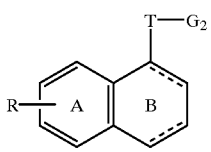
(II/b)

wherein T, A, B, R and $G_2$ are as defined for formula (I), which is subjected to a halogenation reaction when, in the desired compound of formula (I), $G_1$ represents a halogen atom, or which is subjected to an acylation reaction using as reagent an acyl chloride Cl—CO—$R_1$, $R_1$ being as defined for formula (I), to yield a compound of formula (II/c)

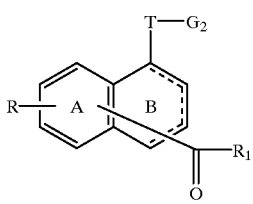
(II/c)

wherein T, A, B, R, $R_1$ and $G_2$ are as defined for formula (I), which can be subjected to a Baeyer-Villiger reaction to yield a compound of formula (I/g):

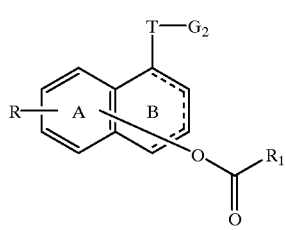

(I/g)

which is a particular case of the compounds of formula (I) wherein T, A, B, R, R$_1$ and G$_2$ are as defined hereinbefore, which, by a hydrolysis reaction, yields a compound of formula (VI)

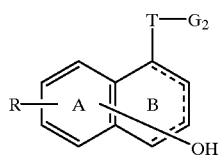

(VI)

wherein T, A, B, R and G$_2$ are as defined for formula (I), the hydroxyl function of which compound of formula (VI) is converted to trifluoromethanesulphonate, using, for example, phenyl bis(trifluoromethanesulphonimide) in a basic medium, to yield a compound of formula (VII):

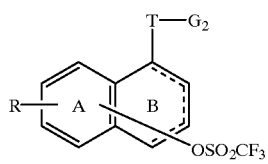

(VII)

which is a particular case of the compounds of formula (I) wherein T, A, B, R and G$_2$ are as defined hereinbefore, which can be converted, via the intermediary of a reaction catalysed by a suitable palladium(0) compound using as reagent a boric acid compound (R$_1$B(OH)$_2$) or a tin compound (R$_1$SnBu$_3$), with R$_1$ being as defined for formula (I), to a compound of formula (I/h):

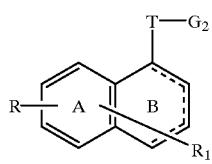

(I/h)

which is a particular case of the compounds of formula (I) wherein T, A, B, R, R$_1$ and G$_2$ are as defined hereinbefore, which compounds of formulae (I/g), (I/h) and (VII),
are purified, if necessary, according to a conventional purification technique,
separated, where appropriate, into their isomers according to a conventional separation technique, and
converted, if desired, into addition salts thereof with a pharmaceutically acceptable acid or base,
which compounds of formulae (I/g) and (I/h), when R represents an O—Alk group (—Alk representing a linear or branched (C$_1$C$_6$)alkyl group), can, when that is compatible with the substituents present on the molecule, be treated with boron tribromide to yield a hydroxylated compound corresponding to formula (VIII):

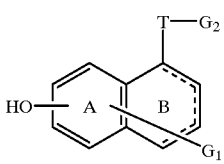

(VIII)

wherein T, A, B, G$_1$ and G$_2$ are as defined for formula (I), the hydroxyl function of which compound (VIII) can be:
converted to trifluoromethanesulphonate to yield a compound of formula (IX):

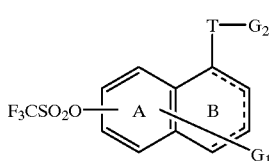

(IX)

which is a particular case of the compound of formula (I), wherein T, A, B, G$_1$ and G$_2$ are as defined hereinbefore, which, via the intermediary of a reaction catalysed by a palladium(0) compound using as reagent a boric acid compound (R'B(OH)$_2$) or a tin compound (R'SnBu$_3$) wherein R' is as defined for formula (I), makes it possible to obtain a compound of formula (I/i):

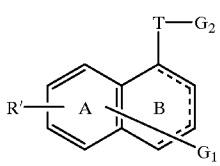

(I/i)

which is a particular case of the compounds of formula (I) wherein T, A, B, R', G$_1$ and G$_2$ are as defined for formula (I), or is subjected to an O-substitution reaction, in a basic medium, using the appropriate halogenated compound as reagent, to yield a compound of formula (I/j):

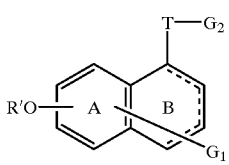

(I/j)

which is a particular case of the compounds of formula (I) wherein T, A, B, R', G$_1$ and G$_2$ are as defined hereinbefore, which compounds of formulae (IX), (I/i) and (I/j):
are purified, if necessary, according to a conventional purification technique,
separated, where appropriate, into their isomers according to a conventional separation technique, and converted, if desired, into addition salts thereof with a pharmaceutically acceptable acid or base.

A G$_1$ group as defined for formula (I) can be converted, when that is useful for the purpose of simplifying the above process, to a different group represented in the description of G$_1$ for formula (I), using conventional reactions of organic chemistry.

The compounds of formulae (I/a) to (I/j) and (II) to (IX) as described in the above process, in which the A and B rings together form a naphthalene group, can be subjected to a reduction reaction, when that is compatible with the substituents present on the molecule, to yield compounds of formula (I) wherein the A and B rings together form a group selected from dihydronaphthalene and tetrahydronaphthalene.

Inversely, aromatisation of the compounds of formulae (I/a) to (I/j) and (II) to (IX) as defined hereinbefore, wherein the A and B rings together form a dihydronaphthalene or tetrahydronaphthalene group, when that is compatible with the substituents present on the molecule, yields naphthalene analogues of formula (I).

The starting materials used in the process described hereinbefore are either commercial or are readily available to the person skilled in the art according to processes well known in the literature.

The compounds of the invention and the pharmaceutical compositions containing them have proved useful in the treatment of disorders of the melatoninergic system.

The pharmacological study of the compounds of the invention has in fact demonstrated that they are atoxic, have a very high selective affinity for melatonin receptors and have substantial activity on the central nervous system and, in particular, therapeutic properties on sleep disorders, anxiolytic, antipsychotic and analgesic properties and properties in respect of microcirculation have been found, enabling it to be established that the compounds of the invention are useful in the treatment of stress, sleep disorders, anxiety, seasonal affective disorders, cardiovascular pathologies, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory losses, Alzheimer's disease, and in cerebral circulation disorders. In another field of activity, the compounds of the invention appear to have ovulation-inhibiting and immunomodulating properties and they appear to be able to be used in the treatment of cancers.

The compounds will preferably be used in the treatment of seasonal affective disorders, sleep disorders, cardiovascular pathologies, insomnia and fatigue due to jetlag, appetite disorders and obesity.

For example, the compounds will be used in the treatment of seasonal affective disorders and sleep disorders.

The present invention relates also to pharmaceutical compositions comprising at least one compound of formula (I) on its own or in combination with one or more pharmaceutically acceptable excipients.

Amongst the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, gelatin capsules, glossettes, lozenges, suppositories, creams, ointments, dermal gels and drinkable or injectable ampoules.

The dosage varies according to the sex, age and weight of the pateint, the route of administration, the nature of the therapeutic indication or associated treatments, and ranges from 0.01 mg to 1 g per 24 hours in 1 or more administrations.

The following Examples illustrate the invention, but do not limit it in any way. The structures of the compounds described have been confirmed by customary spectroscopic techniques.

EXAMPLE 1

N-[2-(7-Methoxy-3-trifluoromethanesulphonyloxy-1-naphthyl)ethyl]acetamide

Step a: N-[2-(3-Acetyl-7-methoxy-1-naphthyl)ethyl] acetamide 0.45 mol (60 g) of aluminium chloride are added at 0° C. to a solution of 0.16 mol (40 g) of N-[2-(7-methoxy-1-naphthyl)ethyl]acetamide (described in Patent EP 447 285) in 350 ml of dichloromethane. 0.21 mol (15.3 ml) of acetyl chloride is then added dropwise at 0° C. The reaction medium is stirred at room temperature for 1 hour and then poured onto ice. The organic phase is decanted and concentrated to yield the expected compound.

Step b: N-[2-(3-Hydroxy-7-methoxy-1-naphthyl)ethyl] acetamide.

0.32 mol (54 g) of meta-chloroperoxybenzoic acid is added to a suspension of 0.16 mol (46 g) of the compound described in the preceding Step in 1.4 litres of dichloromethane. The reaction medium is stirred at room temperature for 20 hours. The mixture is then washed with water, and the excess acid is extracted with a molar solution of sodium hydrogen carbonate. The organic phase is decanted, dried and concentrated. The resulting residue is dissolved in 400 ml of ethanol, and then 500 ml of an aqueous 1 M sodium hydroxide solution are added. After stirring for 1 hour at room temperature, the ethanol is removed by evaporation and the aqueous phase is extracted with 500 ml of dichloromethane. The aqueous phase is then acidified to pH=1, and subsequently extracted with 800 ml of ethyl acetate. The organic phase is concentrated and purified by chromatography on silica gel, using a dichloromethane/methanol mixture, 95/5, as eluant, to yield the expected product.

Step c: N-[2-(7-Methoxy-3-trifluoromethanesulphonyloxy-1-naphthyl)ethyl]acetamide 60 ml of triethylamine are added to a solution of 0.07 mol (18.15 g) of the compound described in the preceding Step in 1 litre of dichloromethane. The reaction mixture is refluxed until solubilisation, and then 0.1 mol (35.8 g) of phenyl bis(trifluoromethanesulphonimide) and 0.75 mol (10.5 g) of potassium carbonate are added. After 4 hours' refluxing, the mixture is washed with 1 litre of 1M sodium hydrogen carbonate and then with 1 litre of 1M hydrochloric acid. The organic phase is dried, concentrated and purified by chromatography on silica gel, using ethyl acetate as eluant, to yield the title product.

| Elemental microanalysis: | | | | |
| --- | --- | --- | --- | --- |
|  | C | H | N | S |
| % Calc. | 49.10 | 4.12 | 3.58 | 8.19 |
| % Found | 48.72 | 4.05 | 3.60 | 8.30 |

EXAMPLE 2

N-[2-(7-Methoxy-3-phenyl-1-naphthyl)ethyl] acetamide 0.1 mol (13.3 g) of phenylboric acid, 1.8 g of palladium(0) tetrakistriphenylphosphine and 5.5 g of lithium chloride are added under an inert atmosphere to a solution of 0.067 mol (24.5 g) of the compound described in Example 1 in 225 ml of dimethoxyethane. The reaction mixture is stirred for 10 minutes and then 160 ml of a molar solution of sodium carbonate and 110 ml of absolute ethanol are added. The reaction mixture is heated at 90° C. for 4 hours. After cooling, 500 ml of 1M sodium carbonate are added, and the reaction mixture is extracted twice with 500 ml of dichloromethane. The organic phase is dried, concentrated and purified by chromatography on silica gel, using ethyl acetate as eluant, to yield the expected compound.

Melting point: 135° C.

EXAMPLE 3

N-[2-(7-Methoxy-3-phenyl-1-naphthyl)ethyl] propionamide

Step a: N-[2-(7-Methoxy-3-trifluoromethanesulphonyloxy-1-naphthyl)ethyl] propionamide The expected product is obtained according to the process described in Example 1, Steps a and b, starting from N-[2-(7-methoxy-1-naphthyl)ethyl]propionamide described in Patent EP 447 285.

Step b: N-[2-(7-Methoxy-3-phenyl-1-naphthyl)ethyl] propionamide

The expected product is obtained according to the process described in Example 2 starting from the compound described in the preceding Step.

EXAMPLE 4

N-[2-(3-Phenyl-1-naphthyl)ethyl]propionamide

The expected product is obtained according to the process described in Example 3 starting from N-(2-(1-naphthyl) ethyl]propionamide described in Patent EP 562 956.

EXAMPLE 5

N-[2-(7-Methoxy-3-phenyl-1-naphthyl)ethyl] cyclopropanecarboxamide

The expected product is obtained according to the process described in Example 3 starting from N-[2-(7-methoxy-1-naphthyl)ethyl]cyclopropanecarboxamide described in Patent EP 447 285.

Example 6

N-[2-(3-Phenyl-1-naphthyl)ethyl] cyclopropanecarboxamide

The expected product is obtained according to the process described in Example 3 starting from N-[2-(1-naphthyl) ethyl]cyclopropanecarboxamide described in Patent EP 562 956.

EXAMPLE 7

N-[2-(7-Methoxy-3-phenyl-1-naphthyl)ethyl] cyclobutanecarboxamide

The expected product is obtained according to the process described in Example 3 starting from N-[2-(7-methoxy-1-naphthyl)ethyl]cyclobutanecarboxamide described in Patent EP 447 285.

EXAMPLE 8

N-[2-(3-Phenyl-1-naphthyl)ethyl] cyclobutanecarboxamide

The expected product is obtained according to the process described in Example 3 starting from N-[2-(1-naphthyl) ethyl]cyclobutanecarboxamide described in Patent EP 562 956.

Melting point: 99° C.
Elemental microanalysis:

|  | C | H | N |
|---|---|---|---|
| % Calc. | 83.86 | 7.04 | 4.25 |
| % Found | 84.09 | 7.16 | 4.53 |

EXAMPLE 9

N-[2-(7-Methoxy-3-phenyl-1-naphthyl)ethyl] butyramide

The expected product is obtained according to the process described in Example 3 starting from N-[2-(7-methoxy-1-naphthyl)ethyl]butyramide described in Patent EP 447 285.

EXAMPLE 10

N-[2-(3-Phenyl-1-naphthyl)ethyl]butyramide

The expected product is obtained according to the process described in Example 3 starting from N-[2-(1-naphthyl) ethyl]butyramide described in Patent EP 562 956.

The compounds of Examples 11 to 27 are obtained according to the process described in Example 2 using the appropriate boric acid compound or tin compound as reagent.

EXAMPLE 11

N-{2-[3-(3-Iodophenyl)-7-methoxy-1-naphthyl] ethyl}acetamide

Melting point: 146° C.
Elemental microanalysis:

|  | C | H | N |
|---|---|---|---|
| % Calc. | 56.64 | 4.53 | 3.15 |
| % Found | 56.79 | 4.69 | 3.30 |

EXAMPLE 12

N-{2-[7-Methoxy-3-(4-methoxyphenyl)-1-naphthyl] ethyl}acetamide

Melting point: 162° C.
Elemental microanalysis:

|  | C | H | N |
|---|---|---|---|
| % Calc. | 75.62 | 6.63 | 4.01 |
| % Found | 75.55 | 6.71 | 3.94 |

EXAMPLE 13

N-{2-[7-Methoxy-3-(3-methoxyphenyl)-1-naphthyl]ethyl}acetamide

Melting point: 109° C.
Elemental microanalysis:

|  | C | H | N |
|---|---|---|---|
| % Calc. | 75.62 | 6.63 | 4.01 |
| % Found | 75.58 | 6.76 | 4.03 |

EXAMPLE 14

N-{2-[7-Methoxy-3-(2-methoxyphenyl)-1-naphthyl]ethyl}acetamide

Melting point: 101° C.
Elemental microanalysis:

|  | C | H | N |
|---|---|---|---|
| % Calc. | 75.62 | 6.63 | 4.01 |
| % Found | 75.62 | 6.80 | 4.01 |

EXAMPLE 15

N-{2-[7-Methoxy-3-(2-trifluoromethyl)phenyl-1-naphthyl]ethyl}acetamide

Melting point: 104° C.
Elemental microanalysis:

|  | C | H | N |
|---|---|---|---|
| % Calc. | 68.21 | 5.20 | 3.62 |
| % Found | 68.22 | 5.48 | 3.62 |

EXAMPLE 16

N-{2-[7-Methoxy-3-(3-trifluoromethyl)phenyl-1-naphthyl]ethyl}acetamide

Melting point: 132° C.
Elemental microanalysis:

|  | C | H | N |
|---|---|---|---|
| % Calc. | 68.21 | 5.20 | 3.62 |
| % Found | 68.37 | 5.30 | 3.68 |

EXAMPLE 17

N-{2-[7-Methoxy-3-(4-trifluoromethyl)phenyl-1-naphthyl]ethyl}acetamide

Melting point: 152° C.
Elemental microanalysis:

|  | C | H | N |
|---|---|---|---|
| % Calc. | 68.21 | 5.20 | 3.62 |
| % Found | 68.23 | 5.02 | 3.59 |

EXAMPLE 18

N-{2-[7-Methoxy-3-(1-naphthyl)-1-naphthyl]ethyl}acetamide

Elemental microanalysis:

|  | C | H | N |
|---|---|---|---|
| % Calc. | 81.27 | 6.27 | 3.71 |
| % Found | 81.23 | 6.43 | 3.79 |

EXAMPLE 19

N-{2-[4-Methoxy-3-(2-naphthyl)-1-naphthyl]ethyl}acetamide

Melting point: 160° C.
Elemental microanalysis:

|  | C | H | N |
|---|---|---|---|
| % Calc. | 81.27 | 6.27 | 3.79 |
| % Found | 80.83 | 6.12 | 3.71 |

EXAMPLE 20

N-{2-[(3-(2-Furyl)-7-methoxy)-1-naphthyl]ethyl}acetamide

Melting point: 138° C.
Elemental microanalysis:

|  | C | H | N |
|---|---|---|---|
| % Calc. | 73.77 | 6.19 | 4.53 |
| % Found | 73.72 | 6.23 | 4.65 |

EXAMPLE 21

N-{2-[(7-Methoxy-3-(2-thienyl))-1-naphthyl]ethyl}acetamide

Melting point: 111° C.
Elemental microanalysis:

|        | C     | H    | N    | S    |
|--------|-------|------|------|------|
| % Calc.  | 70.13 | 5.88 | 4.30 | 9.85 |
| % Found  | 70.05 | 5.92 | 4.30 | 9.73 |

EXAMPLE 22

N-[2-(7-Methoxy-3(4-nitrophenyl)-1-naphthyl)ethyl]acetamide

EXAMPLE 23

N-[2-(7-Methoxy-3-(3-nitrophenyl)-1-naphthyl)ethyl]acetamide

Melting point: 143–144° C.
Elemental microanalysis:

|        | C     | H    | N    |
|--------|-------|------|------|
| % Calc.  | 69.22 | 5.53 | 7.69 |
| % Found  | 69.32 | 5.74 | 7.25 |

EXAMPLE 24

N-[2-(7-Methoxy-3-(2-nitrophenyl)-1-naphthyl)ethyl]acetamide

EXAMPLE 25

N-[2-(3-(4-Aminophenyl)-7-methoxy-1-naphthyl)ethyl]acetamide hydrochloride

EXAMPLE 26

N-[2-(3-(3-Aminophenyl)-7-methoxy-1-naphthyl)ethyl]acetamide hydrochloride

Melting point: 209–210° C.
Elemental microanalysis:

|        | C     | H    | N    | Cl   |
|--------|-------|------|------|------|
| % Calc.  | 68.01 | 6.25 | 7.55 | 9.56 |
| % Found  | 69.19 | 6.23 | 7.55 | 9.45 |

EXAMPLE 27

N-[2-(3-(2-Aminophenyl)-7-methoxy-1-naphthyl)ethyl]acetamide hydrochloride

EXAMPLE 28

N-[2-(3-Formyl-7-methoxy-1-naphthyl)ethyl]acetamide

The expected product is obtained according to the process described in Example 1, Step a, replacing acetyl chloride by dichloromethyl methyl ether.

Melting point: 143–144° C.
Elemental microanalysis:

|        | C     | H    | N    |
|--------|-------|------|------|
| % Calc.  | 70.83 | 6.32 | 5.16 |
| % Found  | 71.11 | 6.36 | 5.26 |

The following positional isomers are also isolated during purification:

N-[2-(4-formyl-7-methoxy-1-naphthyl)ethyl]acetamide
N-[2-(6-formyl-7-methoxy-1-naphthyl)ethyl]acetamide
N-[2-(8-formyl-7-methoxy-1-naphthyl)ethyl]acetamide

EXAMPLE 29

N-[2-(7-Methoxy-4-trifluoromethanesulphonyloxy-1-naphthyl)ethyl]acetamide

Step a: N-[2-(4-Formyl-7-methoxy-1-naphthyl)ethyl]acetamide

The expected product is isolated in the process described in Example 28.

Step b: N-[2-(7-Methoxy-4-trifluoromethanesulphonyloxy-1-naphthyl)ethyl]acetamide The expected product is obtained using the processes described in Steps b and c of Example 1, starting from the compound obtained in the preceding Step.

EXAMPLE 30

N-[2-(7-Methoxy-4-phenyl-1-naphthyl)ethyl]acetamide

The expected product is obtained according to the process described in Example 2, using the compound described in Example 29 as starting material.

The compounds of Examples 31 to 33 are obtained according to the process described in Example 30, using the appropriate boric acid compound or tin compound as reagent.

EXAMPLE 31

N-{2-[4-(2-Furyl)-7-methoxy-1-naphthyl]ethyl}acetamide

EXAMPLE 32

N-{2-[7-Methoxy-4-(2-thienyl)-1-naphthyl]ethyl}acetamide

EXAMPLE 33

N-{2-[7-Methoxy-4-(4-trifluoromethylphenyl)-1-naphthyl]ethyl}acetamide

EXAMPLE 34

N-[2-(7-Methoxy-6-trifluoromethanesulphonyloxy-1-naphthyl)ethyl]acetamide

Step a: N-[2-(6-Formyl-7-methoxy-1-naphthyl)ethyl]acetamide

The expected product is isolated in the course of the process described in Example 28.

Step b: N-[2-(7-Methoxy-6-trifluoromethanesulphonyloxy-1-naphthyl)ethyl]acetamide The expected product is obtained using the processes described in Steps b and c of Example 1, starting from the compound obtained in the preceding Step.

EXAMPLE 35

N-[2-(7-Methoxy-6-phenyl-1-naphthyl)ethyl] acetamide

The expected product is obtained according to the process described in Example 2, using the compound described in Example 34 as starting material.

The compounds of Examples 36 to 39 are obtained according to the process described in Example 35, using the appropriate boric acid compound or tin compound as reagent.

EXAMPLE 36

N-{2-[6-(2-Furyl)-7-methoxy-1-naphthyl]ethyl}acetamide

EXAMPLE 37

N-{2-[7-Methoxy-6-(4-methoxyphenyl)-1-naphthyl]ethyl}acetamide

EXAMPLE 38

N-{2-[7-Methoxy-6-(2-phenyl-1-ethenyl)-1-naphthyl]ethyl}acetamide

EXAMPLE 39

N-[2-(6-Benzyl-7-methoxy-1-naphthyl)ethyl]acetamide

EXAMPLE 40

N-[2-(7-Methoxy-8-trifluoromethanesulphonyloxy-1-naphthyl)ethyl]acetamide

Step a: N-[2-(8-Formyl-7-methoxy-1-naphthyl)ethyl] acetamide

The expected product is isolated in the process described in Example 28.

Step b: N-[2-(7-Methoxy-8-trifluoromethanesulphonyloxy-1-naphthyl)ethyl]acetamide The expected product is obtained using the processes described in Steps b and c of Example 1, starting from the compound obtained in the preceding Step.

EXAMPLE 41

N-[2-(7-Methoxy-8-phenyl-1-naphthyl)ethyl] acetamide

The expected product is obtained according to the process described in Example 2, using the compound described in Example 40 as starting material.

The compounds of Examples 42 and 43 are obtained according to the process described in Example 41, using the appropriate boric acid compound or tin compound as reagent.

EXAMPLE 42

N-{2-[7-Methoxy-8-(2-thienyl)-1-naphthyl]ethyl} acetamide

EXAMPLE 43

N-{2-[7-Methoxy-8-(3-methoxyphenyl)-1-naphthyl) ethyl]acetamide

EXAMPLE 44

N-[2-(7-Hydroxy-3-phenyl-1-naphthyl)ethyl] acetamide 0.04 mol (4.2 ml) of boron tribromide is added to a solution of 0.02 mol (7 g) of the compound described in Example 2 in 200 ml of dichloromethane at 0° C. After 5 hours' stirring at room temperature, the reaction mixture is hydrolysed with ice-cold water and extracted with dichloromethane. The organic phase is dried, concentrated, and purified by chromatography on silica gel to yield the expected compound.

Melting point: 178° C.
Elemental microanalysis:

|  | C | H | N |
|---|---|---|---|
| % Calc. | 78.66 | 6.27 | 4.58 |
| % Found | 78.76 | 6.27 | 4.59 |

EXAMPLE 45

N-[2-(3-Phenyl-7-trifluoromethanesulphonyloxy-1-naphthyl)ethyl]acetamide

The expected product is obtained according to the process described in Example 1, starting from the compound described in Example 44.

Melting point: 128° C.
Elemental microanalysis:

|  | C | H | N | S |
|---|---|---|---|---|
| % Calc. | 57.66 | 4.15 | 3.20 | 7.33 |
| % Found | 57.84 | 4.15 | 3.21 | 7.48 |

EXAMPLE 46

N-[2-(3-Phenyl-1-naphthyl)ethyl]acetamide

The expected product is obtained according to the process described in Example 2, replacing phenylboric acid by formic acid and using the compound described in Example 45 as starting material.

Melting point: 137–139° C.
Elemental microanalysis:

|  | C | H | N |
|---|---|---|---|
| % Calc. | 82.75 | 6.54 | 5.04 |
| % Found | 83.01 | 6.62 | 4.84 |

EXAMPLE 47

N-[2-(3-Phenyl-7-vinyl-1-naphthyl)ethyl]acetamide

The expected product is obtained according to the process described in Example 46, replacing formic acid by tributylvinyltin.

Melting point: 132° C.
Elemental microanalysis:

|         | C     | H    | N    |
|---------|-------|------|------|
| % Calc. | 83.78 | 6.71 | 4.44 |
| % Found | 82.97 | 6.82 | 4.45 |

EXAMPLE 48

N-[2-(7-Ethyl-3-phenyl-1-naphthyl)ethyl]acetamide

A solution of 0.02 mol (7 g) of the compound described in Example 47 in 400 ml of ethanol is stirred under hydrogen atmospheric pressure at room temperature in the presence of 100 mg of palladium-on-carbon for 2 hours. After removal of the catalyst by filtration and removal of the solvent by evaporation, the residue is purified by chromatography on silica gel to yield the expected compound.

Melting point: 130° C.
Elemental microanalysis:

|         | C     | H    | N    |
|---------|-------|------|------|
| % Calc. | 83.24 | 7.30 | 4.41 |
| % Found | 83.08 | 7.55 | 4.47 |

EXAMPLE 49

N-[2-(3-Phenyl-7-propyloxy-1-naphthyl)ethyl]acetamide 0.046 mol (6.3 g) of potassium carbonate is added to a solution of 0.023 mol (7 g) of the compound described in Example 44 in 250 ml of acetone. The reaction mixture is refluxed for 15 minutes, and then 0.046 mol (4.5 ml) of iodopropane is added. The reaction mixture is heated at reflux for 18 hours. After cooling and filtration, the filtrate is concentrated. The residue is taken up in ethyl acetate and extracted, and the organic phase is washed with a 20% sodium hydroxide solution, dried and concentrated to yield the expected compound.

The compounds of Examples 50 to 52 are obtained according to the process described in Example 49 using the appropriate halogenated compound.

EXAMPLE 50

N-[2-(7-Butyloxy-3-phenyl-1-naphthyl)ethyl]acetamide

EXAMPLE 51

N-[2-(7-Hexyloxy-3-phenyl-1-naphthyl)ethyl]acetamide

EXAMPLE 52

N-[2-(7-Cyclopropylmethyloxy-3-phenyl-1-naphthyl)ethyl]acetamide

EXAMPLE 53

N-[2-(3-Carboxy-7-methoxy-1-naphthyl)ethyl]acetamide

A solution of 1.93 mmol (175 mg) of NaClO$_2$ in 2 ml of H$_2$O is added dropwise to a solution of 0.055 mmol (150 mg) of the compound described in Example 28 in 50 ml of acetonitrile and 0.29 mmol (35 mg) of NaH$_2$PO$_4$ in a mixture of 2 ml of water and 0.2 ml of 30% hydrogen peroxide. The reaction mixture is stirred at room temperature for 24 hours and then hydrolysed with an aqueous 1N hydrochloric acid solution. The resulting precipitate is filtered and dried to yield the title compound.

Melting point: 250° C.
Elemental microanalysis:

|         | C     | H    | N    |
|---------|-------|------|------|
| % Calc. | 66.89 | 5.96 | 4.88 |
| % Found | 66.80 | 6.01 | 5.00 |

EXAMPLE 54

N-[2-(3-Iodo-7-methoxy-1-naphthyl)ethyl]acetamide

A solution is formed by adding 46.25 ml of glacial acetic acid and 1.25 ml of concentrated sulphuric acid to 2.5 ml of water. 2.5 g of N-[2-(7-methoxy-1-naphthyl)ethyl] acetamide (10.31 mmol) are dissolved in 30 ml of that solution. 2.09 g of iodine (8.25 mmol) and 0.91 g of HIO$_3$ (5.16 mmol) are then added to the reaction mixture, causing a grey precipitate to appear in a solution that has turned red. The reaction mixture is heated for 15 hours at 65° C., 5.14 ml of concentrated hydriodic acid (13.41 mmol) are added and heating is continued for 2 hours. The suspension is then poured into 200 ml of water and the precipitate that forms is filtered off. The precipitate is dissolved in ethyl acetate and washed with 1M NaHCO$_3$, the organic phase is then concentrated, and purified by chromatography on silica gel, using a dichloromethane/methanol mixture, 99.5/0.5, as eluant, to yield the title product.

Elemental microanalysis:

|         | C     | H    | I     | N    |
|---------|-------|------|-------|------|
| % Calc. | 48.80 | 4.37 | 34.37 | 3.79 |
| % Found | 48.78 | 4.56 | 34.44 | 3.80 |

EXAMPLE 55

N-[2-(7-Phenyl-1-naphthyl)ethyl]acetamide

Step a: N-[2-(7-Hydroxy-1-naphthyl)ethyl]acetamide

The expected product is obtained according to the process described in Example 44, using N-[2-(7-methoxy-1-naphthyl)ethyl]acetamide (described in Patent EP 447 285) as starting material.

Step b: N-[2-(7-Trifluoromethanesulphonyloxy-1-naphthyl)ethyl]acetamide

The expected product is obtained according to the process described in Example 1, using the compound described in the preceding Step as starting material.

Step c: N-[2-(7-Phenyl-1-naphthyl)ethyl]acetamide

The expected product is obtained according to the process described in Example 2, using the compound described in the preceding Step as starting material.

Melting point: 123° C.
Elemental microanalysis:

|  | C | H | N |
|---|---|---|---|
| % Calc. | 83.01 | 6.62 | 4.84 |
| % Found | 82.96 | 6.64 | 4.91 |

The compounds of Examples 56 to 61 are obtained according to the process described in Example 55, Step c, using the appropriate boric acid compound or tin compound.

EXAMPLE 56

N-[2-(7-Vinyl-1-naphthyl)ethyl]acetamide

Melting point: 103° C.
Elemental microanalysis:

|  | C | H | N |
|---|---|---|---|
| % Calc. | 80.30 | 7.16 | 5.85 |
| % Found | 80.50 | 7.32 | 5.94 |

EXAMPLE 57

N-{2-[7-(2-Furyl)-1-naphthyl]ethyl}acetamide

Melting point: 145° C.
Elemental microanalysis:

|  | C | H | N |
|---|---|---|---|
| % Calc. | 77.40 | 6.13 | 5.01 |
| % Found | 78.56 | 6.35 | 5.21 |

EXAMPLE 58

N-{2-[7-(2-Thienyl)-1-naphthyl]ethyl}acetamide

Melting point: 127° C.
Elemental microanalysis:

|  | C | H | N | S |
|---|---|---|---|---|
| % Calc. | 73.19 | 5.80 | 4.74 | 10.85 |
| % Found | 73.28 | 5.77 | 4.82 | 10.78 |

EXAMPLE 59

N-[2-(7-Benzyl-1-naphthyl)ethyl]acetamide

EXAMPLE 60

N-{2-[7-(2-Methoxyphenyl)-1-naphthyl]ethyl}acetamide

Melting point: 107–109° C.

EXAMPLE 61

N-{2-[7-(3-Aminophenyl)-1-naphthyl]ethyl}acetamide hydrochloride

EXAMPLE 62

N-[2-(7-Methoxy-3-trifluoromethanesulphonyloxy-1-naphthyl)ethyl]N'-methylurea

The expected product is obtained according to the process described in Example 1, using N-[2-(7-methoxy-1-naphthyl) ethyl]-N'-methylurea (described in Application EP 530 087) as starting material.

EXAMPLE 63

N-[2-(7-Methoxy-3-phenyl-1-naphthyl)ethyl]-N'-methylurea

The expected product is obtained according to the process described in Example 2, using the compound described in Example 62 as starting material.

The compounds of Examples 64 to 66 are obtained according to the process described in Example 63, using the appropriate boric acid compound or tin compound as reagent.

EXAMPLE 64

N-{2-[3-(2-Furyl)-7-methoxy-1-naphthyl)ethyl]-N'-methylurea

EXAMPLE 65

N-{2-[7-Methoxy-3-(2-thienyl)-1-naphthyl)ethyl]-N'-methylurea

EXAMPLE 66

N-{2-[7-Methoxy-3-(3-methoxyphenyl)-1-naphthyl) ethyl]-N'-methylurea

EXAMPLE 67

N-[2-(7-Methoxy-3-trifluoromethanesulphonyloxy-1-naphthyl)ethyl]N'-propylurea

The expected product is obtained according to the process described in Example 1, using N-[2-(7-methoxy-1-naphthyl) ethyl]-N'-propylurea (described in Patent EP 530 087) as starting material.

EXAMPLE 68

N-[2-(7-Methoxy-3-phenyl-1-naphthyl)ethyl]-N'-propylurea

The expected product is obtained according to the process described in Example 21, using the compound described in Example 67 as starting material.

EXAMPLE 69

N-Methyl-4-(7-methoxy-3-trifluoromethanesulphonyloxy-1-naphthyl)butanamide

The expected product is obtained according to the process described in Example 1, using N-methyl-4-(7-methoxy-1-naphthyl)butanamide (described in Application EP 745 584) as starting material.

EXAMPLE 70

N-Methyl-4-[3-(2-furyl)-7-methoxy-1-naphthyl]butanamide

The expected product is obtained according to the process described in Example 21, using the compound described in Example 69 as starting material and using tributyl(2-furyl)tin as reagent.

The following compounds can be obtained according to processes similar to those described for Examples 69 and 70.

EXAMPLE 71
N-Propyl-4-[3-(2-furyl)-7-methoxy-1-naphthyl]
butanamide

EXAMPLE 72
N-Methyl-4-[7-methoxy-3-(2-pyridyl)-1-naphthyl]
butanamide

The compounds of Examples 73 to 100 are obtained by the reduction, under hydrogen pressure and at a temperature of from 100 to 120° C., of the naphthalene compounds described in the preceding Examples, using a suitable catalyst.

EXAMPLE 73
N-[2-(7-Methoxy-3-phenyl-1,2,3,4-tetrahydro-1-
naphthyl)ethyl]acetamide Melting point: 105–107° C.

EXAMPLE 74
N-[2-(7-Methoxy-3-phenyl-1,2,3,4-tetrahydro-1-
naphthyl)ethyl]cyclopropanecarboxamide

EXAMPLE 75
N-[2-(3-Phenyl-1,2,3,4-tetrahydro-1-naphthyl)ethyl]
cyclopropanecarboxamide

EXAMPLE 76
N-[2-(7-Methoxy-3-phenyl-1,2,3,4tetrahydro-1-
naphthyl)ethyl]butyramide

EXAMPLE 77
N-[2-(3-Phenyl-1,2,3,4-tetrahydro-1-naphthyl)ethyl]
butyramide

EXAMPLE 78
N-{2-[3-(2-Furyl)-7-methoxy-1,2,3,4-tetrahydro-1-
naphthyl]ethyl}acetamide

EXAMPLE 79
N-{2-[7-Methoxy-3-(2-thienyl)-1,2,3,4-tetrabydro-1-
naphthyl]ethyl}acetamide

EXAMPLE 80
N-[2-(7-Ethyl-3-phenyl-1,2,3,4-tetrahydro-1-
naphthyl)ethyl]acetamide

EXAMPLE 81
N-[2-(7-Methoxy-3-(4-methoxyphenyl)-1,2,3,4-
tetrahydro-1-naphthyl)ethyl]acetamide

EXAMPLE 82
N-[2-(7-Methoxy-3-(3-methoxyphenyl)-1,2,3,4-
tetrahydro-1-naphthyl)ethyl]acetamide

EXAMPLE 83
N-[2-(7-Methoxy-3-(3-trifluoromethylphenyl)-1,2,3,
4-tetrahydro-1-naphthyl)ethyl]acetamide

EXAMPLE 84
N-[2-(3-(4-Aminophenyl)-7-methoxy-1,2,3,4-
tetrahydro-1-naphthyl)ethyl]acetamide
hydrochloride

EXAMPLE 85
N-[2-(3-(3-Aminophenyl)-7-methoxy-1,2,3,4-
tetrahydro-1-naphthyl)ethyl]acetamide
hydrochloride

EXAMPLE 86
N-[2-(3-(2-Aminophenyl)-7-methoxy-1,2,3,4-
tetrahydro-1-naphthyl)ethyl]acetamide
hydrochloride

EXAMPLE 87
N-[2-(7-Methoxy-4-phenyl-1,2,3,4-tetrahydro-1-
naphthyl)ethyl]acetamide

EXAMPLE 88
N-{2-[4-(2-Furyl)-7-methoxy-1,2,3,4-tetrahydro-1-
naphthyl]ethyl}acetamide

EXAMPLE 89
N-{2-[7-Methoxy-4-(4-trifluoromethylphenyl)-1,2,3,
4-tetrahydro-1naphthyl]ethyl}acetamide

EXAMPLE 90
N-[2-(7-Methoxy-3-phenyl-1,2,3,4-tetrahydro-1-
naphthyl)ethyl]-N'-methylurea

EXAMPLE 91
N-{2-[3-(2-Furyl)-7-methoxy-1,2,3,4-tetrahydro-1-
naphthyl)ethyl]-N'-methylurea

EXAMPLE 92
N-{2-[7-Methoxy-3-(3-methoxyphenyl)-1,2,3,4-
tetrahydro-1-naphthyl]-ethyl}-N'-methylurea

EXAMPLE 93
N-Methyl-4-[3-(2-furyl)-7-methoxy-1,2,3,4-
tetrahydro-1-naphthyl]-butanamide

EXAMPLE 94
N-[2-(7-Hydroxy-3-phenyl-1,2,3,4-tetrahydro-1-
naphthyl)ethyl]acetamide The expected compound is obtained according to the process described in Example 44 starting from the compound described in Example 73.

The compounds of Examples 95 to 99 are obtained according to the process described in Example 49, using the compound described in Example 101 as starting material and using the appropriate halogenated compound as reagent.

EXAMPLE 95
N-[2-(3-Phenyl-7-vinyloxy-1,2,3,4-tetrahydro-1-
naphthyl)ethyl)acetamide

EXAMPLE 96
N-[2-(3-Phenyl-7-propyloxy-1,2,3,4-tetrahydro-1-
naphthyl)ethyl]acetamide

EXAMPLE 97
N-[2-(7-Butyloxy-3-phenyl-1,2,3,4-tetrahydro-1-
naphthyl)ethyl]acetamide

EXAMPLE 98
N-[2-(7-Hexyloxy-3-phenyl-1,2,3,4-tetrahydro-1-
naphthyl)ethyl]acetamide

EXAMPLE 99
N-[2-(7-Cyclopropyloxy-3-phenyl-1,2,3,4-
tetrahydro-1-naphthyl)ethyl]acetamide The compounds of Examples 100 to 106 are obtained in the same manner as for the compounds of Examples 73 to 93.

EXAMPLE 100
N-[2-(7-Methoxy-3-phenyl-1,2,3,4-tetrahydro-1-
naphthyl)ethyl]cyclobutanecarboxamide

EXAMPLE 101
N-{2-[(1R,3R)and(1S,3S)-7-Methoxy-3-phenyl-1,2,
3,4-tetrahydro-1-naphthyl]
ethyl}cyclobutanecarboxamide Melting point: 141–142° C.

EXAMPLE 102

N-{2-[(1R,3S)and(1S,3R)-7-Methoxy-3-phenyl-1,2,3,4-tetrahydro-1-naphthyl]ethyl}cyclobutanecarboxamide Melting point: 110–111° C.

EXAMPLE 103

N-{2-[(1R,3R)and(1S,3S)-7-Methoxy-3-phenyl-1,2,3,4-tetrahydro-1-naphthyl]ethyl}cyclopropanecarboxamide Melting point: 145° C.

EXAMPLE 104

N-{2-[(1R,3S)and(1S,3R)-7-Methoxy-3-phenyl-1,2,3,4-tetrahydro-1-naphthyl]ethyl}cyclopropanecarboxamide

EXAMPLE 105

N-{2-[(1R,3R)and(1S,3S)-7-Methoxy-3-phenyl-1,2,3,4-tetrahydro-1-naphthyl]ethyl}acetamide

EXAMPLE 106

N-{2-[(1R,3S)and(1S,3R)-7-Methoxy-3-phenyl-1,2,3,4-tetrahydro-1-naphthyl]ethyl}acetamide

EXAMPLE 107

N-[2-(7-Ethyl-3-phenyl-1-naphthyl)ethyl]cyclobutanecarboxamide

Step a: 2-(7-Ethyl-3-phenyl-1-naphthyl)ethylamine 10 ml of an aqueous 20% sodium hydroxide solution are added to a solution of 1.6 mmol (0.5 g) of the compound described in Example 48 in 20 ml of ethanol. The reaction mixture is heated at reflux for 5 hours. After cooling and evaporation, the residue is taken up in a dichloromethane/water mixture and extracted. The organic phase is dried over magnesium sulphate and concentrated to yield the expected compound.

Step b: N-[2-(7-Ethyl-3-phenyl-1-naphthyl)ethyl]cyclobutanecarboxamide 1.6 mmol (0.42 g) of the compound described in the preceding Step are dissolved in a mixture of 8 ml of dichloromethane and 4 ml of water. With vigorous stirring, 4.1 mmol (0.56 g) of potassium carbonate and 1.81 mmol (0.21 g) of cyclobutanoic acid chloride are added in succession at 0° C. The reaction mixture is stirred vigorously at room temperature for 2 hours. The reaction mixture is extracted with dichloromethane and the organic phases are combined, dried over magnesium sulphate and concentrated to yield the expected compound.

| Elemental microanalysis: | | | |
|---|---|---|---|
| | C | H | N |
| % Calc. | 83.99 | 7.61 | 3.92 |
| % Found | 83.44 | 7.62 | 3.99 |

EXAMPLE 108

N-[2-(7-Ethyl-3-phenyl-1-naphthyl)ethyl]trifluoroacetamide

The expected product is obtained according to the process described in Example 107, using trifluoroacetic acid chloride instead of cyclobutanoic acid chloride in Step b.

| Elemental microanalysis: | | | |
|---|---|---|---|
| | C | H | N |
| % Calc. | 71.15 | 5.43 | 3.77 |
| % Found | 71.44 | 5.67 | 3.80 |

EXAMPLE 109

N-[2-(7-Ethyl-3-phenyl-1-naphthyl)ethyl]-3-butenamide

The expected product is obtained according to the process described in Example 107, using vinylacetic acid chloride instead of cyclobutanoic acid chloride in Step b.

| Elemental microanalysis: | | | |
|---|---|---|---|
| | C | H | N |
| % Calc. | 83.93 | 7.34 | 4.08 |
| % Found | 84.36 | 7.21 | 4.22 |

EXAMPLE 110

N-[2-(3-Phenyl-1-naphthyl)ethyl]trifluoroacetamide

Step a: 2-(3-Phenyl-1-naphthyl)ethylamine

The expected product is obtained according to the process described in Example 107, Step a, replacing the compound of Example 48 by the compound described in Example 46.

Step b: N-[2-(3-Phenyl-1-naphthyl)ethyl]trifluoroacetamide

The expected product is obtained according to the process described in Example 107, Step b, using the compound described in the preceding Step as starting material and using trifluoroacetic acid chloride instead of cyclobutanoic acid chloride.

Melting point: 109–110° C.

| Elemental microanalysis: | | | |
|---|---|---|---|
| | C | H | N |
| % Calc. | 69.96 | 4.70 | 4.08 |
| % Found | 69.94 | 4.81 | 4.53 |

EXAMPLE 111

N-[2-(3-Phenyl-1-naphthyl)ethyl]-3-butenamide

The expected product is obtained according to the process described in Example 110, replacing trifluoroacetic acid chloride by vinylacetic acid chloride in Step b.

| | Melting point: 91–92° C. Elemental microanalysis: | | |
|---|---|---|---|
| | C | H | N |
| % Calc. | 83.78 | 6.71 | 4.44 |
| % Found | 83.83 | 6.73 | 4.71 |

EXAMPLE 112

N-(2-{7-Methoxy-3-[3-(trifluoromethyl)phenyl]-1-naphthyl}ethyl)-2-iodoacetamide

The expected product is obtained according to the process described in Example 107, replacing the compound of Example 48 by the compound of Example 16 in Step a, and replacing cyclobutanoic acid chloride by iodoacetic acid chloride in Step b.

| | Elemental microanalysis: | | | |
|---|---|---|---|---|
| | C | H | N | I |
| % Calc. | 51.48 | 3.73 | 2.73 | 24.72 |
| % Found | 51.83 | 3.82 | 2.79 | 24.96 |

The compounds of Examples 113 to 115 are obtained according to the process described in Example 2, using the appropriate boric acid compound or tin compound as reagent.

EXAMPLE 113

N-{2-[7-Methoxy-3-(4-pyridyl)-1-naphthyl]ethyl}acetamide hydrochloride

| | Elemental microanalysis: | | |
|---|---|---|---|
| | C | H | N |
| % Calc. | 67.32 | 5.93 | 7.85 |
| % Found | 67.27 | 5.96 | 7.64 |

EXAMPLE 114

N-{2-[7-Methoxy-3-(3-pyridyl)-1-naphthyl]ethyl}acetamide

| | Melting point: 111–113° C. Elemental microanalysis: | | |
|---|---|---|---|
| | C | H | N |
| % Calc. | 74.98 | 6.29 | 8.74 |
| % Found | 75.05 | 6.59 | 8.75 |

EXAMPLE 115

N-{2-[7-Methoxy-3-(2-pyridyl)-1-naphthyl]ethyl}acetamide

| | Melting point: 150–152° C. Elemental microanalysis: | | |
|---|---|---|---|
| | C | H | N |
| % Calc. | 74.98 | 6.29 | 8.74 |
| % Found | 75.05 | 6.55 | 8.81 |

EXAMPLE 116

N-[2-(3-Cyano-7-methoxy-1-naphthyl)ethyl]acetamide

The expected product is obtained according to the process described in Example 2, replacing phenylboric acid by potassium cyanide.

| | Melting point: 173–175° C. Elemental microanalysis: | | |
|---|---|---|---|
| | C | H | N |
| % Calc. | 71.62 | 6.01 | 10.44 |
| % Found | 71.31 | 6.42 | 10.55 |

EXAMPLE 117

N-[2-(3,7-Diphenyl-1-naphthyl)ethyl]acetamide

The expected product is obtained according to the process described in Example 2, using the compound of Example 45 as starting material.

| | Melting point: 189–190° C. Elemental microanalysis: | | |
|---|---|---|---|
| | C | H | N |
| % Calc. | 85.45 | 6.34 | 3.83 |
| % Found | 85.79 | 6.63 | 4.19 |

The compounds of Examples 118 to 120 are obtained according to the process described in Example 55, Step c, using the appropriate boric acid compound or tin compound.

EXAMPLE 118

N-{2-[7-(4-Methylphenyl)-1-naphthyl]ethyl}acetamide

Melting point: 130–132° C.

EXAMPLE 119

N-{2-[7-(4-Methoxyphenyl)-1-naphthyl]ethyl}acetamide

Melting point: 126–128° C.

EXAMPLE 120

N-{2-[7-(3-Methoxyphenyl)-1-naphthyl]ethyl}acetamide

Melting point: 102–104° C.

EXAMPLE 121

N-[2-(7-Cyano-1-naphthyl)ethyl]acetamide

The expected product is obtained according to the process described in Example 55, Step c, replacing phenylboric acid by potassium cyanide.

Melting point: 158–161° C.
Elemental microanalysis:

|  | C | H | N |
|---|---|---|---|
| % Calc. | 75.61 | 5.92 | 11.76 |
| % Found | 75.86 | 6.01 | 11.56 |

The products of Examples 122 to 127 are obtained using Lawesson's reagent starting from the compounds described in the preceding Examples.

EXAMPLE 122

N-[2-(7-Methoxy-3-phenyl-1-naphthyl)ethyl]thioacetamide

EXAMPLE 123

N-{2-[7-Methoxy-3-(3-methoxyphenyl)-1-naphthyl]ethyl}-thioacetamide

EXAMPLE 124

N-{2-[7-Methoxy-3-(3-aminophenyl)-1-naphthyl]ethyl}thioacetamide

EXAMPLE 125

N-{2-[3-(2-Furyl)-7-methoxy-1-naphthyl]ethyl}thioacetamide

EXAMPLE 126

N-{7-[(4-Methylphenyl)-1-naphthyl]ethyl}thioacetamide

EXAMPLE 127

N-[2-(7-Methoxy-3-phenyl-1,2,3,4-tetrahydro-1-naphthyl)ethyl]thioacetamide

PHARMACOLOGICAL STUDY

EXAMPLE A

Acute toxicity study

The acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

EXAMPLE B

Melatonin receptor binding study on pars tuberalis cells of sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol

1) Sheep pars tuberalis membranes are prepared and used as target tissue in saturation experiments to determine the binding capacities and affinities for 2-[$^{125}$I]-iodomelatonin.
2) Sheep pars tuberalis membranes are used as target tissue in competitive binding experiments using the various test compounds in comparison with melatonin. Each experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

EXAMPLE C

Melatonin $MEL_{1a}$ and $MEL_{1b}$ receptor binding study

The $MEL_{1a}$ or $MEL_{1b}$ receptor binding experiments are carried out using 2-[$^{125}$I]-melatonin as reference radioligand. The radioactivity retained is determined using a Beckman® LS 6000 liquid scintillation counter.

Competitive binding experiments are then carried out in triplicate using the various test compounds. A range of different concentrations is tested for each compound. The results enable the binding affinities of the compounds tested ($IC_{50}$) to be determined.

Thus, the $IC_{50}$ values found for the compounds of the invention show that the binding of the compounds tested is very strong for one or other of the $MEL_{1a}$ and $MEL_{1b}$ receptor sub-types, the values being in a range from 0.1 to 10 nM.

EXAMPLE D

Four plate test

The products of the invention are administered by the oesophagal route to groups each comprising ten mice. One group is given syrup of gum. Thirty minutes after administration of the products to be studied, the animals are placed in cages in which the floor is composed of four metal plates. Each time the animal passes from one plate to another it receives a slight electric shock (0.35 mA). The number of passages from one plate to another in one minute is recorded. After administration, the compounds of the invention significantly increase the number of passages from one plate to another, demonstrating the anxiolytic activity of the compounds of the invention.

EXAMPLE E

Action of the compounds of the invention on the circadian rhythms of locomotive activity of the rat The involvement of melatonin in influencing, by day/night alternation, the majority of physiological, biochemical and behavioural circadian rhythms has made it possible to establish a pharmacological model for research into melatoninergic ligands.

The effects of the molecules are tested on numerous parameters and, in particular, on the circadian rhythms of locomotive activity, which represent a reliable marker of the activity of the endogenous circadian clock.

In this study, the effects of such molecules on a particular experimental model, namely the rat placed in temporal isolation (permanent darkness), are evaluated.

Experimental protocol

One-month-old Long Evans male rats are subjected, as soon as they arrive at the laboratory, to a light cycle of 12 hours of light per 24 hours (LD 12:12). After 2 to 3 weeks' adaptation, they are placed in cages fitted with a wheel connected to a recording system, in order to detect the phases of locomotive activity and thus monitor the nychthemeral (LD) or circadian (DD) rhythms.

As soon as the rhythms recorded show a stable pattern in the light cycle LD 12:12, the rats are placed in permanent darkness (DD).

Two to three weeks later, when the free running (rhythm reflecting that of the endogenous clock) is clearly established, the rats are given a daily administration of the molecule to be tested.

The observations are made by means of visualisation of the rhythms of activity:
 influence on the rhythms of activity by the light rhythm,
 disappearance of the influence on the rhythms in permanent darkness,
 influence by the daily administration of the molecule; transitory or durable effect.

A software package makes it possible:
 to measure the duration and intensity of the activity, the period of the rhythm of the animals during free running and during treatment,
 possibly to demonstrate by spectral analysis the existence of circadian and non-circadian (for example ultradian) components.

Results

The compounds of the invention clearly appear to allow powerful action on the circadian rhythm via the melatoninergic system.

EXAMPLE F

Anti-arrythmic activity

Protocol (Ref: LAWSON J. W. et al. J. Pharmacol. Expert. Therap., 1968, 160, pp. 22–31)

The test substance is administered intraperitoneally to a group of 3 mice 30 minutes before being subjected to anaesthesia with chloroform. The animals are then observed for 15 minutes. The absence of recording of arrythmia and cardiac frequencies higher than 200 beats/min (control: 400–480 beats/min) in at least two animals indicates significant protection.

EXAMPLE G

Pharmaceutical composition: tablets

| | |
|---|---|
| 1000 tablets each comprising 5 mg of the compound of Example 2 | 5 g |
| Wheat starch | 20 g |
| Corn starch | 20 g |
| Lactose | 30 g |

-continued

| | |
|---|---|
| Magnesium stearate | 2 g |
| Silica | 1 g |
| Hydroxypropyl cellulose | 2 g |

We claim:

1. A compound selected from those of formula (I):

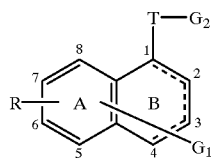

wherein:
A and B together form a naphthalene or tetrahydronaphthalene group,
T represents alkylene having two carbon atoms,
R represents hydrogen, hydroxy, R' or OR', R' representing optionally substituted linear or branched ($C_1$–$C_6$) alkyl, optionally substituted linear or branched ($C_2$–$C_6$) alkenyl, optionally substituted linear or branched ($C_2$–$C_6$)alkynyl, optionally substituted ($C_3$–$C_7$) cycloalkyl, optionally substituted ($C_4$–$C_7$)-cycloalkenyl, linear or branched trihalo($C_1$–$C_6$) alkylsulphonyl, optionally substituted aryl, optionally substituted biphenyl, or optionally substituted heteroaryl,
$G_1$ represents halogen (and in that case is bonded to any of the junctions of the B ring), linear or branched trihalo($C_1$–$C_6$)alkylsulphonyloxy, carboxy, formyl, cyano, or $R_1$, $R_1$ representing optionally substituted aryl, optionally substituted biphenyl or optionally substituted heteroaryl,
$G_2$ represents a group selected from:

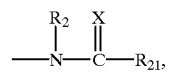
($G_{20}$)

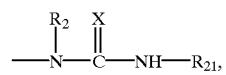
($G_{21}$)

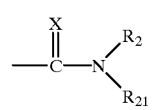
($G_{22}$)

wherein:
X represents oxygen or sulphur,
$R_2$ represents hydrogen,
$R_{21}$ represents optionally substituted linear or branched ($C_1$–$C_6$)alkyl, optionally substituted linear or branched ($C_2$–$C_6$)alkenyl, optionally substituted linear or branched ($C_2$–$C_6$)alkynyl, optionally substituted ($C_3$–$C_7$)cycloalkyl, optionally substituted heteroaryl, optionally substituted aryl, or optionally substituted biphenyl,
with the proviso that:
when $G_2$ represents $G_{22}$, then $G_1$ represents linear or branched trihalo ($C_1$–$C_6$)alkylsulphonyloxy, or optionally substituted heteroaryl different from pyridyl, when A and B together form a tetrahydronaphthalene group, $G_1$ is bonded in the 3- or 4-position of that ring structure, when T represents ethylene and $G_2$ represents $G_{21}$ wherein X represents sulphur, then $R_{21}$ is other than optionally substituted aryl, the term "aryl" denoting phenyl or naphthyl, the term "heteroaryl" denoting mono- or bi-cyclic group having 4 to 11 ring members, being saturated or unsaturated and containing 1 to 4 hetero atoms selected from nitrogen, oxygen, and sulphur, it being understood that:

the term "optionally substituted" applied to the terms "alkyl", "alkenyl", "alkynyl", "cycloalkyl" and "cycloalkenyl" means that those groups are substituted by one or more halogen, and/or ($C_3$–$C_7$)cycloalkyl, hydroxy, linear or branched ($C_1$–$C_6$)alkoxy, optionally substituted aryl, and/or optionally substituted heteroaryl, the term "optionally substituted" applied to the terms "aryl", "biphenyl" and "heteroaryl" means that those groups are substituted by one or more halogen, linear or branched ($C_{1-C6}$)alkyl, linear or branched trihalo ($C_1$–$C_6$)alkyl, hydroxy, linear or branched ($C_1$–$C_6$) alkoxy, and/or nitro, and/or amino (optionally substituted by one or two identical or different linear or branched ($C_1$–$C_6$)alkyl), and/or cyano, carboxy and/or linear or branched ($C_1$–$C_6$)alkylcarbonyl, and/or aminocarbonyl (optionally substituted by one or two identical or different linear or branched ($C_1$–$C_6$)-alkyl), their enantiomers, diastereoisomers, and pharmaceutically-acceptable acid or base addition salts thereof.

2. A compound of claim 1 wherein: $G_1$ is bonded to any of the junctions of the B ring, their enantiomers, diastereoisomers, and pharmaceutically-acceptable acid or base addition salts thereof.

3. A compound of claim 1 wherein:

A and B together form a tetrahydronaphthalene group, and $G_1$ is bonded in the 3- or 4-position of the B ring, their enantiomers, diastereoisomers, and pharmaceutically-acceptable acid or base addition salts thereof.

4. A compound of claim 1 wherein:

A and B together form a naphthalene group,

R represents hydrogen, and $G_1$ is bonded to any of the positions of the A ring, their enantiomers, diastereoisomers, and pharmaceutically-acceptable acid or base addition salts thereof.

5. A compound of claim 1, wherein R is attached in the 7-position of the bicyclic ring structure.

6. A compound of claim 1, wherein $G_1$ is attached in the 3-position of the bicyclic ring structure.

7. A compound of claim 1 wherein $G_1$ is attached in the 7-position of the bicyclic ring structure.

8. A compound of claim 1, wherein $G_1$ represents optionally substituted aryl.

9. A compound of claim 1, wherein $G_1$ represents optionally substituted heteroaryl.

10. A compound of claim 1, wherein R represents R', R' being linear or branched ($C_1$–$C_6$)alkyl or linear or branched ($C_2$–$C_6$)alkenyl.

11. A compound of claim 1, wherein R represents OR', R' being linear or branched ($C_1$–$C_6$)alkyl or linear or branched ($C_2$–$C_6$)alkenyl.

12. A compound of claim 1, wherein $G_2$ is such that X represents oxygen, $R_2$ represents hydrogen, and $R_{21}$ represents a group selected from linear or branched ($C_1$–$C_6$)alkyl optionally substituted by one or more halogen, linear or branched ($C_2$–$C_6$)alkenyl, linear or branched ($C_2$–$C_6$) alkynyl, and ($C_3$–$C_7$)cycloalkyl.

13. A compound of claim 2 wherein R, which is attached in the 7-position of the bicyclic ring structure, represents R' or OR', R' being linear or branched ($C_1$–$C_6$)alkyl or linear or branched ($C_2$–$C_7$)alkenyl, $G_1$ is attached in the 3-position of the bicyclic ring structure, and $G_2$ represents $G_{20}$ or G22 wherein X represents oxygen, $R_2$ represents hydrogen, and $R_2$ represents a group selected from linear or branched ($C_1$–$C_6$)alkyl optionally substituted by one or more halogen, linear or branched ($C_2$–$C_6$)alkenyl, linear or branched ($C_2$–$C_6$)alkynyl and ($C_3$–$C_7$)cycloalkyl.

14. A compound of claim 3 wherein R, which is attached in the 7-position of the bicyclic ring structure, represents R' or OR', R' being linear or branched ($C_1$–$C_6$)alkyl or linear or branched ($C_2$–$C_7$)alkenyl, $G_1$ is attached in the 3-position of the bicyclic ring structure and represents a group selected from optionally substituted aryl and optionally substituted heteroaryl, and $G_2$ represents $G_{20}$ or $G_{22}$ wherein X represents oxygen, $R_2$ represents hydrogen, and $R_{21}$ represents a group selected from linear or branched ($C_1$–$C_6$)alkyl optionally substituted by one or more halogen, linear or branched ($C_2$–$C_6$)alkenyl, linear or branched ($C_2$–$C_6$)alkynyl, and ($C_3$–$C_7$)cycloalkyl.

15. A compound of claim 4 wherein $G_1$ is attached in the 7-position of the bicyclic ring structure and represents optionally substituted aryl or optionally substituted heteroaryl, and $G_2$ represents $G_{20}$ or $G_{22}$ wherein X represents oxygen, $R_2$ represents hydrogen, and $R_{21}$ represents a group selected from linear or branched ($C_1$–$C_6$)alkyl optionally substituted by one or more halogen, linear or branched ($C_2$–$C_6$)alkenyl, linear or branched ($C_2$–$C_6$)alkynyl, and ($C_3$–$C_7$)cycloalkyl.

16. A compound of claim 1 which is N-[2-(7-methoxy-3-phenyl-1-naphthyl)ethyl] acetamide.

17. A compound of claim 1 which is N-{2-[7-methoxy-3-(3-trifluoromethylphenyl)-1-naphthyl]ethyl}acetamide.

18. A compound of claim 1 which is selected from N-{2-[7-methoxy-3-(3-aminophenyl)-1-naphthyl]ethyl}acetamide and its addition salts with a pharmaceutically-acceptable acid.

19. A compound of claim 1 which is selected from:

N-{2-[3-(2-furyl)-7-methoxy-1-naphthyl] ethyl}acetamide and

N-{2-[7-methoxy-3-(4-pyridyl)-1-naphthyl] ethyl}acetamide.

20. A compound of claim 1 which is selected from:

N-[2-(7-phenyl-1-naphthyl)ethyl]acetamide and

N-{2-[7-(4-methylphenyl)-1-naphthyl]ethyl}acetamide.

21. A compound of claim 1 which is selected from:

N-[2-(7-methoxy-3-phenyl-1,2,3,4-tetrahydro-1-naphthyl)ethyl]acetamide and

N-{2-[7-methoxy-3-(3-trifluoromethylphenyl)-1,2,3,4-tetrahydro-1-naphthyl]ethyl}acetamide.

22. A pharmaceutical composition 1 in the treatment of diseases associated with the melatoninergic system comprising as active principle an effective amount of a compound as claimed in claim 1, together with one or more pharmaceutically-acceptable excipients or vehicles.

23. A method for treating a living body afflicted with a disease associated with the melatoninergic system comprising the step of administering to the living body an amount of a compound of claim 1 which is effective for alleviation of said disease.

* * * * *

UNITED STATES PATENT AND TRADEMARK OFFICE
CERTIFICATE OF CORRECTION

PATENT NO. : 6,143,789
DATED : November 7, 2000
INVENTOR(S) : F. Lefoulon, L. Demuynck D. Lesieur, P. Depreux, C. Bennejean, P. Renard, P. Delagrange.

Page 1 of 2

It is certified that error appears in the above-identified patent and that said Letters Patent is hereby corrected as shown below:

Column 2, line 33: "$(C_1\text{-}c_6)$" should read: -- $(C_1\text{-}C_6)$ --. Page 3, line 10

Column 6, line 64: At the beginning of the line, "$R_2$" should read: -- $R_{21}$ --. Page 9, line 6

Column 9, line 38(approx): "$G_1$" should read: -- $G_3$ --. Page 13, line 5

Column 19, line 3: Insert "}" at the end of the line. Page 25, line 22

Column 19, line 4: Delete "}" at the beginning of the line.

Column 27, line 34: "-tetrabydro-1-" at the end of the line, should read: -- -tetrahydro-1- --. Page 38, line 1

Column 36, line 23: At the end of the line, "$(C_{1\text{-}c6})$" should read: -- $(C_1\text{-}C_6)$ --. Page 51, line 8

Column 37, line 23: "$(C_{1\text{-}c6})$" should read: -- $(C_1\text{-}C_6)$ --. Page 54, line 8

UNITED STATES PATENT AND TRADEMARK OFFICE
CERTIFICATE OF CORRECTION

PATENT NO. : 6,143,789
DATED : November 7, 2000
INVENTOR(S) : F. Lefoulon, L. Demuynck D. Lesieur, P. Depreux, C. Bennejean, P. Renard, P. Delagrange Page 2 of 2

It is certified that error appears in the above-identified patent and that said Letters Patent is hereby corrected as shown below:

Column 37, line 35: After the word "wherein:", insert the following: -- A and B together form a naphthalene group, and --. Page 54, line 16

The line beginning "$G_1$. . ." should start a new line.

Column 38, line 11: "$R_2$" should read: -- $R_{21}$ --. Page 58, line 22

Column 38, line 57(approx): "1" in the middle of the sentence should be deleted, and replaced with: -- useful --. Page 60, line 8

Signed and Sealed this

Eighth Day of May, 2001

Attest:

NICHOLAS P. GODICI

Attesting Officer

Acting Director of the United States Patent and Trademark Office